US008322221B1

(12) United States Patent
Sathish et al.

(10) Patent No.: US 8,322,221 B1
(45) Date of Patent: Dec. 4, 2012

(54) NON-CONTACT HIGH RESOLUTION NEAR FIELD ACOUSTIC IMAGING SYSTEM

(75) Inventors: Shamachary Sathish, Bellbrook, OH (US); John T. Welter, Fairborn, OH (US); Kumar V. Jata, Yellow Springs, OH (US); Richard Reibel, Dayton, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 400 days.

(21) Appl. No.: 12/411,826

(22) Filed: Mar. 26, 2009

(51) Int. Cl.
*G01N 9/24* (2006.01)
*G01N 29/04* (2006.01)

(52) U.S. Cl. ............................................ 73/606; 73/608
(58) Field of Classification Search ............... 73/606, 73/607
See application file for complete search history.

(56) References Cited

U.S. PATENT DOCUMENTS

| | | | | |
|---|---|---|---|---|
| 4,333,345 A * | 6/1982 | Renzel et al. | ................... | 73/606 |
| 4,350,045 A * | 9/1982 | Chow et al. | ................... | 73/607 |
| 4,554,836 A | 11/1985 | Rudd | | |
| 4,991,442 A | 2/1991 | Matsumoto | | |
| 5,520,052 A * | 5/1996 | Pechersky | ................... | 73/579 |
| 5,679,899 A | 10/1997 | Webster et al. | | |
| 5,801,312 A * | 9/1998 | Lorraine et al. | ................ | 73/602 |
| 6,186,004 B1 | 2/2001 | Kaduchak et al. | | |
| 6,236,049 B1 * | 5/2001 | Thomas et al. | ............ | 250/341.6 |
| 6,320,665 B1 | 11/2001 | Ngoi et al. | | |
| 6,396,195 B1 * | 5/2002 | Lindblad et al. | ......... | 310/323.19 |
| 6,715,354 B2 | 4/2004 | Wooh | | |
| 6,786,098 B2 * | 9/2004 | Bates | ............................. | 73/606 |
| 6,844,936 B2 | 1/2005 | Dalhoff | | |
| 6,877,894 B2 * | 4/2005 | Vona et al. | ...................... | 374/45 |
| 6,880,379 B2 * | 4/2005 | Hedberg et al. | .............. | 73/12.01 |

(Continued)

OTHER PUBLICATIONS

D.A. Hutchins et al., "Lamb-Wave Tomography using Non-Contact Transduction", Ultrasonics, 1993, vol. 31 No. 2, pp. 97-101.

(Continued)

*Primary Examiner* — Lisa Caputo
*Assistant Examiner* — Jamel Williams
(74) *Attorney, Agent, or Firm* — AFMCLO/JAZ; Fredric Sinder

(57) ABSTRACT

A non-contact near field high resolution acoustic imaging system of a sample, the system including an acoustic wave generator generating a plurality of acoustic waves a ultrasonic horn amplifying the waves to an amplitude of between about 20 microns and about 300 microns, and a frequency between about 20 kHz and about 40 khz. The ultrasonic horn further directs the amplified waves to impinge upon the sample. On contact between the waves and the sample, a plurality of transmitted energy is transmitted to the sample, a plurality of longitudinal displacements and surface acoustic wave displacements in the sample are created. An adjustable separation distance lies between the sample and the ultrasonic horn, the distance adjusted to maximize the transmitted energy. The distance is preferably greater than the maximum displacement of the ultrasonic horn, or approximately 0.1 mm. The non-contact near field high resolution acoustic imaging system further includes a surface displacement detector for detecting the longitudinal wave displacements or surface acoustic wave displacements, the detector including a tip and a tip diameter; and a computer for digitizing and storing the longitudinal wave displacements or surface acoustic wave displacements. The longitudinal displacements or surface acoustic wave displacements are analyzed to create an image of at least a portion of the sample, the image alternatively having a resolution about equal to the surface displacement detector tip diameter.

6 Claims, 1 Drawing Sheet

U.S. PATENT DOCUMENTS

| | | | |
|---|---|---|---|
| 6,907,799 | B2 | 6/2005 | Jacobsen et al. |
| 6,998,616 | B2* | 2/2006 | Favro et al. .................. 250/341.6 |
| 7,060,971 | B2* | 6/2006 | Zombo et al. ............... 250/252.1 |
| 7,064,331 | B2* | 6/2006 | Rothenfusser et al. .... 250/341.6 |
| 7,073,384 | B1 | 7/2006 | Donskoy et al. |
| 7,114,393 | B2 | 10/2006 | Langdon |
| 7,131,331 | B2* | 11/2006 | Bates ............................. 73/589 |
| 7,146,846 | B2 | 12/2006 | Mahaffey et al. |
| 7,716,987 | B2* | 5/2010 | Sathish et al. ................. 73/589 |
| 2006/0144902 | A1* | 7/2006 | Pochardt et al. ............. 228/101 |
| 2008/0022775 | A1* | 1/2008 | Sathish et al. ................. 73/606 |
| 2009/0000382 | A1* | 1/2009 | Sathish et al. ................. 73/606 |

OTHER PUBLICATIONS

M. Clark et al., "Non-Contact Acoustic Microscopy", Meas. Sci. Technol., 2000, vol. 11, pp. 1792-1801.

J.D. Fox et al., "Acoustic Microscopy in Air at 2 MHz", Appl. Phys. Lett., Sep. 1, 1985, vol. 47 (5), pp. 465-467.

T. Enzure et al., "Optical Measurement of Sound Fields Estimated from Multiple Interference Images using Mach-Zehnder Interferometer", Electronics and Communications in Japan, Part 2, 2004, vol. 87, No. 11, pp. 1324-1330.

M. Clark et al., "Fast, All-Optical Rayleigh Wave Microscope: Imaging on Isotropic and Anisotropic Materials", IEEE Transactions on Ultrasonics, Ferroelectrics, and Frequency Control, Jan. 2000, vol. 47 No. 1, pp. 65-73.

K.S. Ho et al., "Application of Pulse Compression Signal Processing Techniques to Electromagnetic Acoustic Transducers for Noncontact Thickness Measurements and Imaging", Review of Scientific Instruments, 2005, vol. 76, 054902.

S.D. Sharples et al., "Fast Noncontact Imaging of Material Microstructure using Local Surface Acoustic Wave Velocity Mapping", IEEE Ultrasonics Symposium, 2005, pp. 886-889.

C.A. DiMarzio et al., "Toward a Laser-Based, Non-Contact Acoustic Landmine Imager", Proceedings of SPIE, 2000, vol. 4038, pp. 740-747.

S.D. Sharples et al., "Spatially Resolved Acoustic Spectroscopy for Fast Noncontact Imaging of Material Microstructure", Optics Express, Oct. 30, 2006, vol. 14, No. 22, 10435.

C. Miyasaka et al., "Recent Advances in Acoustic Microscopy for Nondestructive Evaluation", Transactions of the ASME, Aug. 2000, vol. 122, pp. 374-378.

T.W. Murray et al., "Multiplexed Interferometer for Ultrasonic Imaging Applications", Opt. Eng., Jul. 2001, vol. 40(7), pp. 1321-1328 ( ).

\* cited by examiner

NON-CONTACT HIGH RESOLUTION NEAR FIELD ACOUSTIC IMAGING SYSTEM

RIGHTS OF THE GOVERNMENT

The invention described herein may be manufactured and used by or for the Government of the United States for all governmental purposes without the payment of any royalty.

BACKGROUND OF THE INVENTION

The invention relates to a high resolution non-contact near field acoustic imaging system for nondestructive evaluation and testing of materials and components.

During the last decades, several nondestructive techniques based on acoustic wave propagation have been developed for evaluation and testing of materials and components. The ability of acoustic waves to penetrate into the interior of the material has been utilized to obtain critical information about the life-limiting defects in materials as well as components. Acoustic wave propagation has found applications in metals, ceramics, composites, biological and other materials for Non-Destructive Examination (NDE). Often in acoustic testing, the acoustic waves are excited in the material by placing an ultrasonic transducer in direct contact. A coupling medium like water, oil, grease or thin solid material is used between the transducer and the material to provide the direct contact. As the acoustic waves propagate through the material, defects along the path reflect/scatter the acoustic waves. The reflected/scattered signals are detected using the same ultrasonic transducer [pulse-echo] or by placing another transducer on an opposite side, or on the same side in contact with the material [thru transmission]. While this technique allows examination of individual locations, it is extremely time consuming to obtain an image of larger structures. Moreover, the spatial resolution is determined by the diameter of the transducer. In order to enhance the resolution and ease the restriction on scanning, focused acoustic beam techniques in the presence of water were developed. These techniques are known C-scan, C-SAM, and Scanning Acoustic Microscopy. In these methods, the acoustic waves are focused on or in the interior of the test material in the presence of water. The reflected/transmitted signals are detected by a focused transducer, gated, amplified, digitized and stored in a computer. The transducer or the sample may be raster scanned and an acoustic image is constructed using the stored amplitude data. The spatial resolution depends on the acoustic wavelength in water. Typically at 100 MHz the resolution is about 15 µm through water. Utilizing frequencies of the order of 2 GHz, a resolution of about 0.5 µm may be obtained.

Apart from using longitudinal and shear waves, surface acoustic waves (Rayleigh, Lamb, etc.) have been used. The Rayleigh waves propagate on the surface of the material. They penetrate to about one wavelength into the material. The Rayleigh waves are very sensitive to near surface defects. On the other hand, Lamb waves propagate in the entire thickness of the plate. They are also known as plate waves. The Lamb waves are very useful in examining larger structures.

In the acoustic testing methods of thru-transmission and pulse-echo methods, the excitation and detection are separated by several wavelengths of sound distance. The received signal is typically an average over this distance. When the distance between the scattering defect and the receiver is much larger than several wavelengths, the system is known to operate in far field. In general, in far field operation the spatial resolution is limited by the wavelength of the sound as described by Rayleigh criteria. This is also applicable to the C-scan, C-SAM, and acoustic microscopic methods of evaluation where the resolution has been increased by merely focusing the acoustic waves. Instead of operating in the far field, if the instrument can be operated in the near field the resolution is not limited by the wavelength of sound and instead it is determined by the diameter of the sensor.

Focused acoustic beams operating at higher frequencies provide higher spatial resolution. At high frequencies the penetration depth dramatically decreases, minimizing the advantage of in-depth evaluation of the material. Although, acoustic techniques are routinely used for nondestructive evaluation and testing, the material has to be immersed in a fluid, often water. To overcome the water contact problem, specialized air coupled ultrasonic transducers (both unfocused and focused) have been developed as discussed in M. C. Bharadwaj, et al., "Non Contact Ultrasound: Final Frontier in nondestructive materials characterization," Ceramic Engineering and Science Proceedings, $24^{th}$ Annual Conference on Composites, Advanced ceramics, Materials and structures: Ed. T. Jensen and E. Ustundag, The American Ceramic Society, Westerville, Ohio (2000). All documents herein referenced are incorporated by reference.

Air coupled ultrasonic transducers operate in air at frequencies in the range of a few hundred kHz to about 5 MHz. The acoustic waves generated by these transducers propagate through air are incident on the sample surface. A large amount of the acoustic energy is reflected, while a small amount will pass through the material. The transmitted signal is detected by another air coupled transducer. There is significant loss of acoustic energy at the sample air interface, because of huge acoustic impedance mismatch between the solid material and air. Thus, the received signal requires an enormous amount of amplification. It also requires significant signal processing to detect the acoustic signal that travels through the material. Although this is a significant improvement, the spatial resolution is limited by the diameter of the transducer and operating frequencies. In fact, the receiving transducer has the same size as the transmitting transducer. It is well known that the amplitude of the received signal is directly proportional to the diameter of the transducer. Thus larger diameter transducers are often used in the experiments. The air coupled ultrasonic imaging has found several applications both in material evaluation and testing as well as in biomedical applications, because it can be performed in air.

In the present invention, we combine the advantages of air coupled transduction and a localized optical detection with a laser interferometer. The acoustic waves in air are excited using an air coupled ultrasonic horn or air coupled ultrasonic transducer. The acoustic waves propagate through the sample and include reflected signals which are detected using non-contacting methods. These non-contacting methods may include but are not limited to a fiber optic displacement sensor or a laser interferometer. The acoustic displacement signal from the optical detector is amplified and stored digitally in the computer. The data at different locations is obtained by a raster scanning a sample in the x and y directions. An acoustic image of the material is built with the stored data.

Another method of complete non-contact acoustic imaging is with the help of laser generated acoustic waves and laser based detection systems. In these methods a high intensity laser periodically impacts the surface of the sample. Due to thermoelastic conversion, an acoustic wave is generated in the material. The propagating acoustic waves cause surface displacements and are detected by a laser interferometer at any other location. By scanning the excitation laser and the detecting interferometer, an acoustic image is developed. The laser ultrasonic methods have high resolution and are completely non contact in nature. One of the major problems with the methodology is the need for high amplitude pulsed lasers for generation of acoustic waves. The possibility of surface damage caused by the high power lasers due to ablation or other heat induced effects may be a limitation of this technique.

SUMMARY OF THE INVENTION

A non-contact near field high resolution acoustic imaging system of a sample, the system including an acoustic wave generator generating a plurality of acoustic waves, an ultrasonic horn amplifying the waves to an amplitude of between about 20 microns and about 300 microns, and a frequency between about 20 kHz and about 40 khz. The ultrasonic horn further directs the amplified waves to impinge on the sample. On contact between the waves and the sample, a plurality of transmitted energy is transmitted to the sample, a plurality of longitudinal displacements and surface acoustic wave displacements in the sample are created. An adjustable separation distance lies between the sample and the ultrasonic horn, the distance adjusted to maximize the transmitted energy. The distance is preferably greater than the maximum displacement of the ultrasonic horn, or approximately 0.1 mm. The non-contact near field high resolution acoustic imaging system further includes a surface displacement detector for detecting the longitudinal wave displacements or surface acoustic wave displacements, the detector having a tip and a tip diameter; and a computer for digitizing and storing the longitudinal displacements or surface acoustic wave displacements. The longitudinal displacements or surface acoustic wave displacements are analyzed to create an image of at least a portion of the sample, the image preferably having a resolution of the diameter of the surface displacements detector. The surface displacements detector tip diameter is preferably less than about 2 mm.

DETAILED DESCRIPTION

Figure 1:
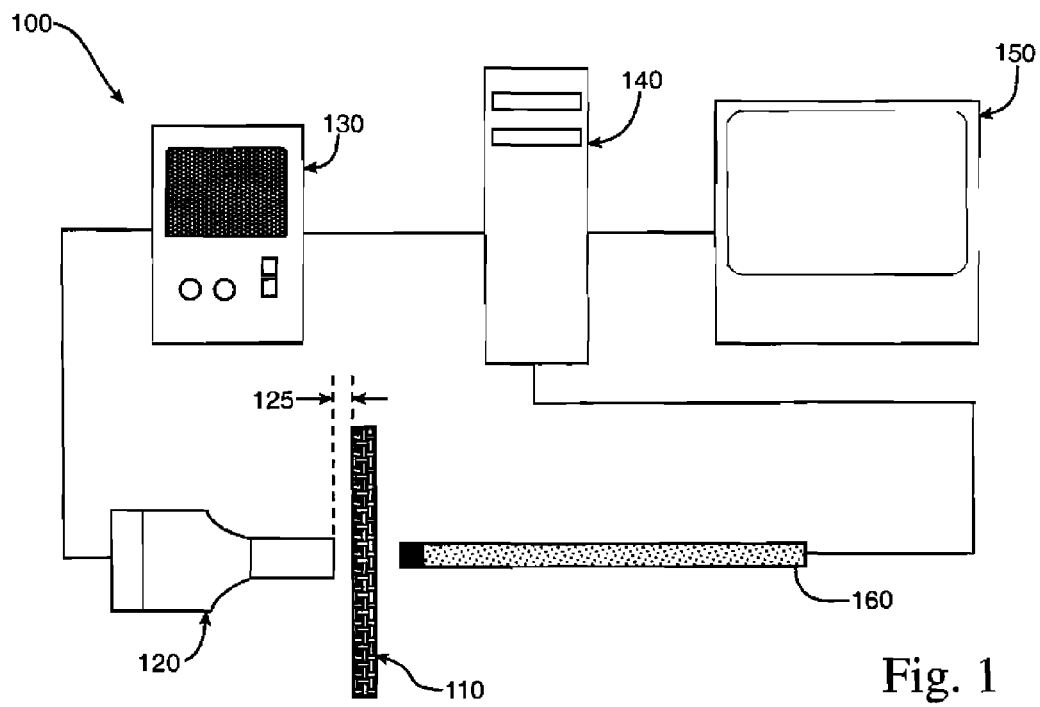
FIG. 1 is an illustration of one embodiment of the present invention.
Figure 2:
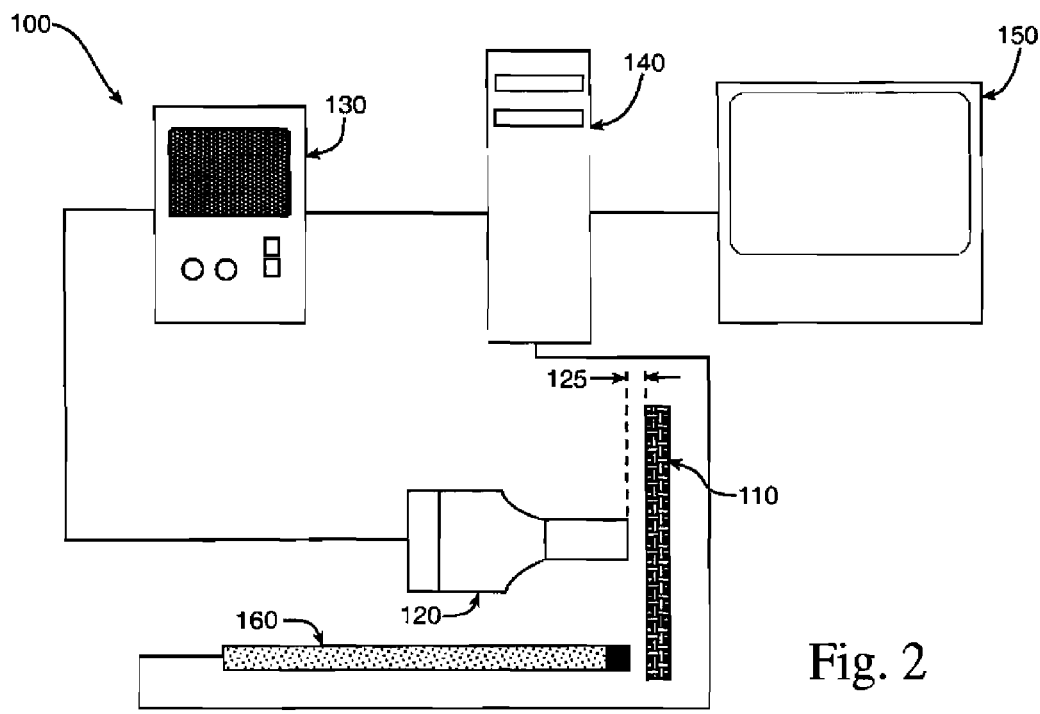
FIG. 2 is an illustration of another embodiment of the present invention.

FIGS. 1 and 2 show two illustrations of an embodiment of a non-contact near field high resolution acoustic imaging system 100 of a sample 110. The components of the system include an acoustic wave generator 130, a surface displacement detector 160, an ultrasonic horn 120, a computer 140 with an optional display 150. The ultrasonic horn 120 is an adjustable separation distance 125 from the sample 110. In FIG. 1 the surface displacement detector 160 is placed with the sample 110 between it and the ultrasonic horn 120. Alternatively, the surface displacement detector 160 may be placed on the same side of the sample 110 as the ultrasonic horn 120 as shown in FIG. 2. The surface displacement detector 160 preferably has a tip with a tip diameter 161 of between about 0.2 mm and about 8 mm, between about 0.5 mm and about 5 mm, or alternatively between about 1 mm and about 2 mm.

The acoustic wave generator 130 may include a stack of piezoelectric transducers to generate 20 KHz acoustic waves, although other frequencies may be used. The principle of stacking a series of transducers is to obtain significant high amplitude acoustic waves. The acoustic amplitude may be further amplified with the help of an ultrasonic horn such as an acoustic horn. The amplitude of the acoustic waves from the acoustic horn may be up to several hundred microns, alternatively about 100 µm to about 700 µm, alternatively more than 750 µm, alternatively about 20 µm to about 300 µm.

The ultrasonic horn 120 and the piezoelectric stack together may alternatively be an air coupled ultrasound transducer that operates at about 1 MHz or more. Alternatively the air coupled ultrasound operates between about 1 MHz and about 5 MHz. The surface displacement detector 160 may alternatively be a laser vibrometer with a sensitivity of preferably at least 5 microns.

The sample to be tested may be placed at a small distance from the end of the acoustic horn, preferably at least about 20 µm or a distance greater than expected displacement of the acoustic horn, whichever ensures the sample remains in non-contact with the acoustic horn through the excitation. The plurality of high amplitude acoustic waves impinges on the sample. The sample reflects part of the energy and transmits some of the energy. The transmitted energy can be optimized by adjusting the distance between the sample and the horn. Acoustic waves impacting the material can produce longitudinal waves through the material and also surface acoustic waves that propagate along the surface of the material. The longitudinal waves propagating through the material produce longitudinal displacements on the opposite side of the sample as shown in FIG. 1. The surface acoustic waves produced on the sample 110 surface cause displacements and can be detected by the surface displacement detector 160 as shown in FIG. 2. The surface displacement detector may be any detector known in the art, including an optical detector or laser vibrometer.

These surface displacements are normal to the plane of the sample surface and are detected using the surface displacement detector 160. The sample surface does not need to be particularly flat or smooth. One example of a surface displacement detector is a fiber optic displacement sensor placed at an appropriate distance from the surface of the sample. The fiber optic displacement sensor consists of a set of fibers to illuminate the surface of the material, and the reflected light is detected by another set of optical fibers. The detected signal is carried to a photodetector for measurement. The amplitude of the reflected light is proportional to the surface displacement. The amplitude of the signal from the optical fiber is further amplified, digitized and stored in a computer. The diameter of the entire optical fiber detector is approximately a few hundred microns in the embodiment, although other diameters are envisioned. While keeping the acoustic horn and the fiber optic displacement sensor at a fixed position, the sample may be raster scanned to scan a larger surface area of the sample. Alternatively, the acoustic horn and fiber optic displacement sensor could be raster scanned and the sample held stationary. Amplitude data at each location may be stored in a computer and an acoustic image may be developed from the data collected.

Alternatively, the surface displacement detector may be a laser interferometer detector with a spot diameter of about 5 µm to about 10 µm.

The spatial resolution of the instrument system depends on the diameter of the surface displacement detector that detects and measures the acoustic amplitude and not on the frequency of the acoustic waves. The wavelength of the acoustic waves in most materials at 20 KHz is several orders of magnitude larger than the diameter of surface displacement detector. The wavelength of the acoustic wave in air is also extremely large compared to the diameter of surface displacement detector and the adjustable distance. These conditions make the instrument operate as a near field imaging system.

The high amplitude acoustic transducer is a (Branson) ultrasonic welding unit. The surface displacement detector may be a commercially available vibration sensor (Philtec Inc., etc.). The spatial resolution of the instrument in such a configuration is in the range of a few hundred microns, which is equal to the diameter of the surface displacement detector. The distance between the specimen and the surface displacement detector is alternatively between 0.01 mm and 5 mm. The surface displacement detector may be replaced by a commercially available laser interferometer [Polytec] to increase the spatial resolution to a few microns. The adjustable separation distance between the specimen and the ultrasonic horn is in the range of 1-2 millimeters. The adjustable separation distance may be less than 1 millimeter, but the adjustable separation distance must be greater than the displacement of the ultrasonic horn. The adjustable separation distance may be extended through optimization up to about 5 millimeters or even greater. The laser interferometer may be any interferometer or vibrometer known in the art such as a Polytec interferometer or a scanning laser vibrometer.

Although the instrument may be used in general for non-contact nondestructive evaluation of materials and components, the major impact is expected to be in the area of polymers, sheet metals and components. Another important application is in the electronic and micro-electronic industry where immersion of components in water should be avoided.

What is claimed is:

1. A non-contact near field high resolution acoustic imaging system for investigating a sample, the system including:
    an acoustic wave generator for generating a plurality of acoustic waves;
    an ultrasonic horn for directing the waves to impinge on the sample, whereby on contact between the waves and the sample energy will be transmitted to the sample, and longitudinal displacements and surface acoustic wave displacements in the sample are created;
    an adjustable separation distance between the sample and the ultrasonic horn, the distance adjustable for maximizing the transmitted energy, and the distance being greater than the maximum displacement of the ultrasonic horn;
    a surface displacement detector for detecting the longitudinal wave displacements or surface acoustic wave displacements, the surface displacement detector having a tip with a tip diameter between about 0.2 mm and about 8 mm; and,
    a computer for digitizing and storing successively detected longitudinal displacements or surface acoustic wave displacements, whereby the longitudinal displacements or surface acoustic wave displacements can be analyzed to create a raster scan image of at least a portion of the sample, the image having a resolution equal to the tip diameter.

2. The non-contact near field high resolution acoustic imaging system of claim 1 wherein the surface displacement detector is a laser with a sensitivity greater than about 5 μm.

3. The non-contact near field high resolution acoustic imaging system of claim 1 wherein the ultrasonic horn is an air coupled ultrasound transducer that operates at about 1 MHz.

4. The non-contact near field high resolution acoustic imaging system of claim 1 wherein the ultrasonic horn is an air coupled ultrasound transducer that operates at more than 1 MHz.

5. The non-contact near field high resolution acoustic imaging system of claim 1 wherein the surface displacement detector is a laser interferometer or scanning laser vibrometer.

6. A method for creating a high resolution acoustic image of a sample, the method including:
    generating at least one high amplitude acoustic wave;
    creating a plurality of longitudinal displacements and transmitted energy by propagating the acoustic waves through the sample;
    adjusting a separation distance between the sample and a transducer to maximize the transmitted energy wherein the adjustable separation distance is greater than the maximum longitudinal displacement of the ultrasonic horn;
    successively detecting the longitudinal displacements of the waves that went through the sample or surface acoustic wave displacements of waves propagating on the surface of the sample using a displacement detector having a tip with a tip diameter between about 0.2 mm and about 8 mm; and,
    creating a raster scan image of a portion of the sample using the successively detected longitudinal displacements or the surface acoustic wave displacements, the image having a resolution equal to the tip diameter.

* * * * *